United States Patent
Son et al.

(10) Patent No.: US 10,836,912 B2
(45) Date of Patent: Nov. 17, 2020

(54) GLOSSY PIGMENT HAVING HOLLOW STRUCTURE AND METHOD FOR PRODUCING SAME

(71) Applicant: CQV CO., LTD., Chungcheongbuk-do (KR)

(72) Inventors: Yong-Ho Son, Cheongju-si (KR); Kwang-Choong Kang, Cheongju-si (KR); Byung-Ki Choi, Cheongju-si (KR); Kwang-Soo Lim, Chungcheongbuk-do (KR); Kil-Wan Chang, Cheongju-si (KR)

(73) Assignee: CQV CO., LTD, Chungcheongbuk-Do (KR)

( * ) Notice: Subject to any disclaimer, the term of this patent is extended or adjusted under 35 U.S.C. 154(b) by 189 days.

(21) Appl. No.: 15/765,371

(22) PCT Filed: Sep. 30, 2016

(86) PCT No.: PCT/KR2016/010966
§ 371 (c)(1),
(2) Date: Apr. 2, 2018

(87) PCT Pub. No.: WO2017/082537
PCT Pub. Date: May 18, 2017

(65) Prior Publication Data
US 2018/0298198 A1      Oct. 18, 2018

(30) Foreign Application Priority Data
Nov. 11, 2015   (KR) .................. 10-2015-0157873

(51) Int. Cl.
C09C 1/36        (2006.01)
C09D 7/40        (2018.01)
(Continued)

(52) U.S. Cl.
CPC .......... *C09C 1/3692* (2013.01); *A61K 8/0245* (2013.01); *A61K 8/29* (2013.01);
(Continued)

(58) Field of Classification Search
None
See application file for complete search history.

(56) References Cited

U.S. PATENT DOCUMENTS 4,040,859 A * 8/1977 Esselborn ............. C09C 1/0021
106/417
4,192,691 A    3/1980 Armanini
(Continued)

FOREIGN PATENT DOCUMENTS

CN      1628155 A        6/2005
CN    103462140 A   *   12/2013
(Continued)

OTHER PUBLICATIONS

Japanese Office Action for corresponding Japanese Application No. 2018-520166 dated May 28, 2019.
(Continued)

*Primary Examiner* — Colleen P Dunn
*Assistant Examiner* — Ross J Christie
(74) *Attorney, Agent, or Firm* — Hauptman Ham, LLP

(57) ABSTRACT

Disclosed are a glossy pigment having a hollow structure and a method for producing the same. The glossy pigment having a hollow structure according to the present invention comprises: a hollow which penetrates through the center of the inside thereof; and a metal oxide coating layer which covers a part or all of the hollow, wherein the metal oxide coating layer has a hollow structure having a thickness of 0.1-3 μm.

10 Claims, 1 Drawing Sheet

(51) Int. Cl.
*C09C 3/06* (2006.01)
*C09C 1/00* (2006.01)
*A61K 8/02* (2006.01)
*A61K 8/29* (2006.01)
*A61K 8/96* (2006.01)

(52) U.S. Cl.
CPC ............ *A61K 8/965* (2013.01); *C09C 1/0021* (2013.01); *C09C 1/363* (2013.01); *C09C 1/3653* (2013.01); *C09C 3/06* (2013.01); *C09D 7/40* (2018.01); *A61K 2800/436* (2013.01); *C01P 2004/30* (2013.01); *C01P 2004/61* (2013.01); *C01P 2004/62* (2013.01); *C01P 2006/10* (2013.01); *C01P 2006/32* (2013.01)

(56) References Cited

U.S. PATENT DOCUMENTS

| | | |
|---|---|---|
| 5,076,849 A | 12/1991 | Vapaaoksa et al. |
| 5,611,851 A | 3/1997 | DeLuca et al. |

FOREIGN PATENT DOCUMENTS

| | | |
|---|---|---|
| EP | 0377326 A1 | 7/1990 |
| EP | 0761773 A2 | 3/1997 |
| EP | 0912640 B1 | 3/2000 |
| JP | 55-60565 A | 5/1980 |
| JP | 2-263871 A | 10/1990 |
| JP | 9-194757 A | 7/1997 |
| JP | 2001-172118 A | 6/2001 |
| JP | 2002-338424 A | 11/2002 |
| JP | 2007-520598 A | 7/2007 |
| JP | 2009-234854 A | 10/2009 |
| JP | 2013-100518 A | 5/2013 |
| JP | 5513364 B2 | 6/2014 |
| KR | 1020010073979 A | 8/2001 |
| KR | 1020050002857 A | 1/2005 |
| KR | 1020050006253 A | 1/2005 |
| KR | 101180040 B1 | 8/2012 |
| WO | 2003076526 A1 | 9/2003 |
| WO | 2008114744 A1 | 9/2008 |

OTHER PUBLICATIONS

Extended European Search Report for corresponding PCT Application No. PCT/KR2016010966 dated Jun. 24, 2019.
International Search Report for Application No. PCT/KR2016/010966 dated Jan. 19, 2017.
Chinese Office Action dated Dec. 4, 2019 corresponding to Chinese Application No. 201680062255.8.

* cited by examiner

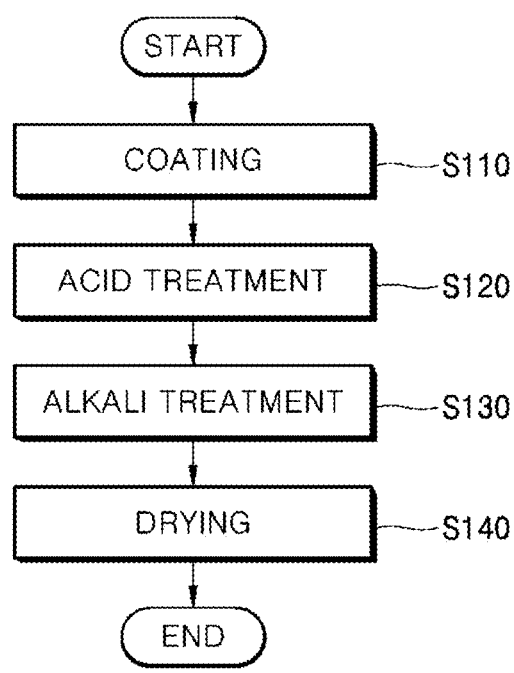

GLOSSY PIGMENT HAVING HOLLOW STRUCTURE AND METHOD FOR PRODUCING SAME

TECHNICAL FIELD

The present invention relates to a glossy pigment and a method for producing the same, and more particularly, to a glossy pigment having a hollow structure and a method for producing the same.

BACKGROUND ART

The high-refractive pearlescent light functional materials are the advanced products that are increasingly demanded according to the trend of high quality design for automobile, cosmetics and all industry fields presently in the world.

Such high refractive pearlescent light functional materials are widely used for industrial purposes such as a wallpaper, a mat, a plastic product, a leather coating, an accessory, a silk printing, a toy, a home appliance, ceramics and a building material, and for cosmetics purposes such as a lipstick, a manicure, a hair gel, a cosmetics package, color cosmetics, and a food contact container, an automobile painting, construction materials that require high weather resistance, a photocatalyst, an electromagnetic shield, and a prevention of tampering of securities.

A mica is largely used to make the high refractive pearlescent light functional materials. That is, the mica coated with a metal oxide has an interference color or a coloring effect depending on the kind of the metal oxide, and also, reflects or scatters the light, and exhibits a soft gloss. Therefore, various studies have been actively conducted on the method of coating the metal oxide of the mica for obtaining a desired property by using a property of the mica.

A related art is Korean Patent Laid-Open Publication No. 10-2001-0073979 (published on Aug. 4, 2001), which discloses a method for producing a pearlescent pigment by coating the metal oxide on a synthetic mica.

DISCLOSURE

Technical Problem

It is an object of the present invention to provide a glossy pigment having a hollow structure capable of reducing the weight by forming an empty hollow by completely removing a plate type flake base material and a method for producing the same.

Technical Solution

A method for producing a glossy pigment having a hollow structure in accordance with an exemplary embodiment of the present invention is characterized in comprising: (a) coating a metal oxide on a plate type flake base material to form a metal oxide coating layer, (b) after an acid treatment primarily by adding an acidic solution in a state mixing the plate type flake base material formed with the metal oxide coating layer, with deionized water and suspending it, reflux washing and filtering it; (c) after an alkali treatment secondarily by adding a basic solution in a state of mixing dehydrated water with the dehydrated washed resultant and suspending it, after step (b), refluxing and filtering it; (d) drying the resultant of step (c) to obtain a metal oxide coating layer having a hollow structure removed with the plate type flake base material.

The glossy pigment having the hollow structure in accordance with an exemplary embodiment of the present invention for achieving the object is characterized in including a hollow which penetrates through the center of an inside thereof, a metal oxide coating layer which covers a part or all of the hollow, wherein the metal oxide coating layer has a hollow structure having a thickness of 0.1 to 3 μm.

Advantageous Effects

A glossy pigment having a hollow structure according to the present invention and the method for producing the same is subjected to the secondary alkali treatment in a state where a part of the plate type flake base material is removed by the primary acid treatment, it is possible to completely remove the plate type flake base material. It can have an empty hollow structure, and the weight is light, and it also has a hollow structure, thereby securing excellent concealment and shielding performance.

Accordingly, in the case of the glossy pigment having the hollow structure produced by the method according to the present invention, it can be widely used for industrial purposes such as a wallpaper, a mat, a plastic product, a leather coating, an accessory, a silk printing, a toy, a home appliance, ceramics and a building material, and for cosmetics purposes such as a lipstick, a manicure, a hair gel, a cosmetics package, color cosmetics, and a food contact container, an automobile painting, construction materials that require high weather resistance, a photocatalyst, an electromagnetic shield, and a prevention of tampering of securities

DESCRIPTION OF DRAWINGS

FIG. 1 is a process flowchart illustrating a method of producing a glossy pigment having a hollow structure in accordance with an exemplary embodiment of the present invention.

BEST MODE

The advantages, the features of the present invention and the method of achieving them will become apparent with reference to the embodiments described in detail below together with the accompanying drawings. However, the present invention may be embodied in many different forms and is not limited to the embodiments disclosed below. Rather, the present embodiments are provided so that the disclosure of the present invention will be complete, and it will fully convey the scope of the invention to those skilled in the art to which the present invention pertains. The present invention is merely defined by the scope of claims. Like reference numerals refer to like elements throughout the specification.

Hereinafter, a glossy pigment having a hollow structure according to a preferred embodiment of the present invention and a method for producing the same will be described in detail with reference to the accompanying drawings.

FIG. 1 is a process flowchart illustrating a method for producing a glossy pigment having a hollow structure in accordance with an exemplary embodiment of the present invention.

Referring to FIG. 1, a method for producing a glossy pigment having a hollow structure in accordance with an exemplary embodiment of the present invention includes a coating step S110, an acid treatment step S120, a base treatment step S130, and a drying step S140.

Coating

In the coating step (S110), a metal oxide is coated on a plate type flake base material to form a metal oxide coating layer.

At this time, the plate type flake base material may include at least one selected from a mica, plate type silica and glass flake, and it is most preferable to use the mica. With regard to the mica, a synthetic mica or a natural mica may be both used, but most preferably a synthetic mica can be used. Such the plate type flake base material can be used with the pulverized and classified powders, or it can be used by pulverizing or classifying it after producing the powders.

It is preferable that the plate type flake base material has a mean diameter of 10 to 150 μm. When the mean diameter of the plate type flake base material is less than 10 μm, an aspect ratio is decreased due to the fact that the material is coated on the surface of the plate type flake base material and the plate type flake base material gradually becomes a sphere as the coating thickness increases. When the aspect ratio is reduced, it causes scattering of light due to a diffused reflection, and there is a problem which does not exhibit the same color having the same refractive index constantly. On the contrary, when the mean diameter of the plate type flake base material exceeds 150 μm, the surface area to be coated increases, and thus, it may be difficult to form a coating layer for embodying a color.

The metal oxide may include at least one selected from $TiO_2$, $SiO_2$, $Al_2O_3$, $ZrO_2$ and $SnO_2$. At this time, it is preferable that the metal oxide has a mean diameter of 10 to 100 nm. When the mean diameter of the metal oxide is less than 10 nm, it may be difficult to coat the metal oxide on the plate type flake base material. On the other hand, when the mean diameter of the metal oxide exceeds 100 nm, it is difficult to expect a glossy effect by a light scattering.

At this time, it is preferable that the metal oxide coating layer is formed to a thickness of 0.1 to 3 μm. When the thickness of the metal oxide coating layer is less than 0.1 μm, an infrared reflection effect may be slight. On the contrary, when the thickness of the metal oxide coating layer exceeds 3 μm, it may act as a factor for increasing the producing cost only without any further effect increase, which is not economical.

Acid Treatment

In an acid treatment step (S120), after an acidic solution was added and primarily acid treated in a state of mixing a plate type flake base material formed with a metal oxide coating layer with deionized water and suspending it, it was reflux washed and filtered.

At this time, it is more preferable to apply an ultrasonic wave at an output power condition of 15 to 40 kHz and 70 to 110 W while stirring at a speed of 300 to 500 rpm.

When a stirring speed is less than 300 rpm or the ultrasonic output power is less than 70 W, the stirring may be insufficient. On the contrary, when the stirring speed exceeds 500 rpm or the ultrasonic output power exceeds 110 W, the particles are severely broken and a generation of the unnecessary small-sized particles is increased, making it difficult to control the size to a desired size or proceeded a subsequent process.

At this time, any one selected from sulfuric acid, phosphoric acid, and nitric acid may be used alone, as the acidic solution, or a mixed solution mixed with at least two of them may be used. It is preferable that such an acid solution is diluted to a concentration of 40 to 60 wt %. When the concentration of the acidic solution is less than 40 wt %, the plate type flake base material does not dissolve well during the primary acid treatment, and thus, it may be difficult to secure the hollow structure. On the contrary, when the concentration of the acidic solution exceeds 60 wt %, it may cause a problem that the coated metal oxide coating layer together with the plate type flake base material may be dissolved together due to an excessive concentration.

In this step, it is preferable that a reflux is carried out at 80 to 120° C. for 4 to 6 hours. When a reflux temperature is less than 80° C. or a reflux time is less than 4 hours, a sufficient dissolution rate cannot be secured and a surface crack can be caused by an insoluble plate type flake due to a formation of an uneven hollow sphere. On the contrary, when the reflux temperature exceeds 120° C. or the reflux time exceeds 6 hours, the cracking of the hollow sphere coating layer or a separation of the metal oxide coating layer may occur due to the stirring, which is not preferable.

Base Treatment

In the base treatment step (S130), after a basic solution was added and secondarily base treated in a state of mixing deionized water with a hydrated washed resultant and suspending it after the acid treatment step (S120), it was refluxed and filtered.

As the basic solution, it is preferable to use a strong base at a concentration of 40 to 55% by weight, and specifically, at least one selected from sodium hydroxide and potassium hydroxide may be used.

When the concentration of the basic solution is less than 40% by weight, there is a problem that the plate type flake base material coated with the primarily acid-treated metal oxide layer may not be completely dissolved and the hollow shape may not be formed. On the contrary, when the concentration of the basic solution exceeds 55% by weight, it is not preferable since the plate type flake base material as well as the coated metal oxide layer can be dissolved together due to the excessive concentration.

At this time, it is preferably that the reflux is performed at 50 to 70° C. for 1 to 3 hours.

In the present invention, since the secondary alkali treatment is performed in a state which removes more than half of the plate type flake base material by a primary acid treatment by adding sulfuric acid to the plate type flake base material formed with the metal oxide coating layer, it is possible to completely remove all the plate type flake base material so that it can produce the glossy pigment to have an empty hollow structure.

Drying

In the drying step (S140), the resultant of the base treatment step (S130) is dried to obtain a metal oxide coating layer of a hollow structure removed with the plate type flake base material.

At this time, it is preferable that the drying is performed at 100 to 150° C. for 10 to 120 minutes. When the drying temperature is less than 100° C. the drying time may be prolonged and an economy and a productivity may be degraded. On the contrary, when the drying temperature exceeds 150° C., an agglomeration may increase between the powder particles, which is undesirable.

The glossy pigment having the hollow structure produced in the above-described processes (S110 to S140) has a hollow which penetrates through the center of an inside thereof and a metal oxide coating layer covering a part or all of the hollow. At this time, it is preferable that the metal oxide coating layer is formed to be a thickness of 0.1 to 3 μm. When the thickness of the metal oxide coating layer is out of the above range, a reflection effect is slight and a gloss efficiency may not be good.

At this time, since the glossy pigment having the hollow structure produced by the method in accordance with an exemplary embodiment of the present invention is subjected to the secondary alkali treatment in a state where a part of the plate type flake base material is removed by the primary acid treatment, it is possible to completely remove the plate type flake base material. It can have an empty hollow structure, and the weight is light, and it also has a hollow structure, thereby securing excellent concealment and shielding performance.

Accordingly, in the case of a glossy pigment having a hollow structure produced by the method according to the present invention, it may be widely used for industrial purposes such as a wallpaper, a mat, a plastic product, a leather coating, an accessory, a silk printing, a toy, a home appliance, ceramics and a building material, and for cosmetics purposes such as a lipstick, a manicure, a hair gel, a cosmetics package, color cosmetics, and a food contact container, an automobile painting, construction materials that require high weather resistance, a photocatalyst, an electromagnetic shield, and a prevention of tampering of securities.

EXAMPLES

Hereinafter, a configuration and an action of the present invention will be described in more detail via the preferred embodiments of the present invention. It is provided by way of example only and is not to be construed as limiting the invention in any meaning.

The contents which are not described here are sufficiently technically judged to those skilled in the art, and a description thereof will be omitted.

1. Production of Glossy Pigment

Example 1

200 ml of deionized water and 100 g of a mica coated with $TiO_2$ were added in a 3 flask (Morton Flask) and suspended. Next, after a condenser was mounted in a reactor, 400 ml of $H_2SO_4$ was added and it was stirred at 400 rpm.

Next, it was refluxed for 6 hours while maintaining it at 100° C., cooled, and then 800 ml of water was added and refluxed again. Then, it was filtered using Filter Paper, and then washed four times with 1000 ml of water.

Next, the acid-treated powder was added to a 3 L flask, and 800 ml of deionized water was added thereto. It was stirred at a speed of 400 rpm and suspended, and 400 ml aqueous solution of NaOH in a concentration of 50 wt % was added, and then, it was refluxed for 4 hours while maintaining 60° C.

Thereafter, it was filtered using the filter paper, washed with 800 ml of water four Limes, and dried at 120° C. to prepare a glossy pigment having a hollow structure.

Example 2

A glossy pigment having a hollow structure was prepared in the same manner as in Example 1 except that an aqueous NaOH solution having a concentration of 40 wt % was used.

Example 3

A glossy pigment having a hollow structure was prepared in the same manner as in Example 1 except that a 45 wt % aqueous solution of KOH was used instead of the aqueous solution of NaOH at a concentration of 50 wt %.

Example 4

A glossy pigment having a hollow structure was prepared in the same manner as in Example 1, except that 400 ml of $H_2SO_4$ was added and stirred at 350 rpm and the ultrasonic waves were applied in a condition at a frequency of 30 kHz and an output power of 100 W.

Example 5

A glossy pigment having a hollow structure was prepared in the same manner as in Example 1, except that 400 ml of $H_2SO_4$ was added and stirred at 450 rpm and the ultrasonic waves were applied in a condition at a frequency of 25 kHz and an output power of 90 W.

Comparative Example 1

200 ml of deionized water and 100 g of mica coated with $TiO_2$ were added in a 3 L flask (Morton Flask) and were suspended. Next, after a condenser was mounted in a reactor, 400 ml of $H_2SO_4$ was added and it was stirred at 350 rpm.

Then, it was refluxed for 6 hours while maintaining it at 90° C., was cooled, and 800 ml of water was added and refluxed again. Then, it was filtered using a filter paper, washed with 1000 ml of water four times, and dried at 120° C. to prepare a glossy pigment.

Comparative Example 2

A glossy pigment was prepared in the same manner as in Comparative Example 1, except that 400 ml of $H_2SO_4$ was added thereto, stirred at 450 rpm, and refluxed for 5 hours while maintaining 110° C.

Comparative Example 3

A glossy pigment was prepared in the same manner as in Comparative Example 1, except that 400 ml of $H_2SO_4$ was added and stirred at 350 rpm and the ultrasonic waves were applied in a condition at a frequency of 30 kHz and an output power of 100 W.

2. Property Evaluation

Table 1 shows the physical property evaluation results for the glossy pigments prepared according to Examples 1 to 5 and Comparative Examples 1 to 3.

1) Density

With regard to the density measurements of the samples of Examples 1 to 5 and Comparative Examples 1 to 3, after measuring the weight of Examples 1 to 5 and Comparative Examples 1 to 3 by using a Pycnometer (AccuPyc 1330) product of Micromeritics Co., Ltd, the sample was added in a 4.0 cc flask, and then He gas was injected to find the true density which the sample takes, and the specific gravity was measured.

2) Thermal Conductivity

The measurement was performed with a laser flash analysis (LFA) equipment. A fluid cell in a small circular plate made of aluminum was filled with the samples of Examples 1 to 5 and Comparative Examples 1 to 3, and the laser was projected and heated on one side of the sample, and the time the heat was transferred to the opposite side was measured with an infrared sensor.

TABLE 1

| Classification | Density (g/ml) | Thermal conductivity (mW/m · K) |
| --- | --- | --- |
| Example 1 | 0.72 | 77 |
| Example 2 | 0.87 | 89 |

TABLE 1-continued

| Classification | Density (g/ml) | Thermal conductivity (mW/m · K) |
|---|---|---|
| Example 3 | 0.82 | 81 |
| Example 4 | 0.51 | 72 |
| Example 5 | 0.53 | 74 |
| Comparative Example 1 | 3.45 | 347 |
| Comparative Example 2 | 3.41 | 339 |
| Comparative Example 3 | 2.79 | 326 |

As shown in Table 1, it can be seen that the densities of Examples 1 to 5 are significantly lower than those of Comparative Examples 1 to 3. In particular, it can be seen that the densities of Examples 4 and 5 in which the ultrasonic treatment was performed were respectively measured at the significantly low values.

In addition, in Examples 1 to 5, it was confirmed that the thermal conductivities were lower than those in Comparative Examples 1 to 3, indicating that a heat insulating performance was excellent.

At this time, in the case of Comparative Examples 1 to 3 in which only the acid treatment was performed without performing the base treatment, the hollow density was measured to be a considerably large value. Therefore, it is considered that the inside thereof was not completely removed even if it has a hollow form.

Based on the above experimental results, it has been confirmed that the first acid treatment and the second base treatment can produce a glossy pigment having a hollow structure which is light and having excellent heat insulating performance.

Hereinabove, while the present invention has described in connection with the embodiments of the present invention, various changes or modifications can be made in a level of those skilled person in the art to which the present invention pertains. These changes and modifications belong to the present invention unless departing from the scope of the technical idea which the present invention provides. Accordingly, the scope of the present invention should be considered by the following claims.

The invention claimed is:

1. A method of producing a glossy pigment having a hollow structure, comprising:
    (a) coating a metal oxide on a plate type flake base material to form a metal oxide coating layer;
    (b) performing an acid treatment, wherein the acid treatment comprises:
        treating the plate type flake having the coating layer with an acid solution; and
        applying an ultrasonic wave to the plate type flake having the coating layer and the acid solution while stirring at a speed of 300 rpm to 500 rpm, wherein the ultrasonic wave has a frequency ranging from 15 kHz to 40 kHz and an output power ranging from 70 w to 110 W;
    (c) after an alkali treatment secondarily by adding a basic solution in a state of mixing dehydrated water with the dehydrated washed resultant and suspending it, after step (b), refluxing and filtering it;
    (d) drying the resultant of step (c) to obtain a metal oxide coating layer having a hollow structure removed with the plate type flake base material.

2. The method of producing a glossy pigment having a hollow structure of claim 1,
    in step (a),
    the plate type flake base material comprises at least one selected from a mica, plate type silica, and glass flake.

3. The method of producing a glossy pigment having a hollow structure of claim 1, wherein the metal oxide comprises at least one selected from $TiO_2$, $SiO_2$, $Al_2O_3$, $ZrO_2$ and $SnO_2$.

4. The method of producing a glossy pigment having a hollow structure of claim 1,
    in step (b),
    the acid solution is a mixed solution of any one or two or more selected from sulfuric acid, phosphoric acid, and nitric acid.

5. The method of producing a glossy pigment having a hollow structure of claim 1, further comprises: after step (b),
    (b') refluxing the acid treated plate type flake having the coating layer in deionized water, wherein the reflux is performed at 80 to 120° C. for 4 to 6 hours.

6. The method of producing a glossy pigment having a hollow structure of claim 1,
    in step (c),
    the basic solution comprises at least one selected from sodium hydroxide, and potassium hydroxide.

7. The method of producing a glossy pigment having a hollow structure of claim 1,
    in step (c),
    the reflux is performed at 50 to 70° C. for 1 to 3 hours.

8. The method of producing a glossy pigment having a hollow structure of claim 1,
    in step (d),
    the drying is performed at 100 to 150° C. for 10 to 120 minutes.

9. The glossy pigment having a hollow structure which is produced by the method of producing the glossy pigment described in claim 1, comprising:
    a hollow which penetrates through a center of the inside thereof; and
    a metal oxide coating layer which covers a part or all of the hollow;
    wherein the metal oxide coating layer has a thickness of 0.1 to 3 μm.

10. A cosmetic composition containing a glossy pigment having a hollow structure, which is produced by the method described in claim 1.

* * * * *